(12) United States Patent
Munoz et al.

(10) Patent No.: US 7,332,516 B2
(45) Date of Patent: Feb. 19, 2008

(54) GEMINALLY DI-SUBSTITUTED NSAID DERIVATIVES AS Aβ42 LOWERING AGENTS

(75) Inventors: Benito Munoz, San Diego, CA (US); Petpiboon Prasit, Rancho Santa Fe, CA (US); Nicholas Simon Stock, San Diego, CA (US)

(73) Assignee: Merck + Co., Inc., Rahway, NJ (US)

( * ) Notice: Subject to any disclaimer, the term of this patent is extended or adjusted under 35 U.S.C. 154(b) by 109 days.

(21) Appl. No.: 10/540,601

(22) PCT Filed: Jan. 9, 2004

(86) PCT No.: PCT/US2004/000424

§ 371 (c)(1),
(2), (4) Date: Jun. 23, 2005

(87) PCT Pub. No.: WO2004/064771

PCT Pub. Date: Aug. 5, 2004

(65) Prior Publication Data

US 2006/0063937 A1     Mar. 23, 2006

Related U.S. Application Data

(60) Provisional application No. 60/439,847, filed on Jan. 14, 2003, provisional application No. 60/439,965, filed on Jan. 14, 2003.

(51) Int. Cl.
| | | |
|---|---|---|
| *A61K 21/421* | (2006.01) | |
| *A61K 31/41* | (2006.01) | |
| *A61K 31/403* | (2006.01) | |
| *A61K 31/404* | (2006.01) | |
| *A61K 31/4035* | (2006.01) | |
| *A61K 31/381* | (2006.01) | |
| *A61K 31/38* | (2006.01) | |
| *A61K 31/192* | (2006.01) | |

(52) U.S. Cl. ............... 514/375; 514/381; 514/411; 514/418; 514/419; 514/429; 514/431; 514/448; 514/569; 514/570

(58) Field of Classification Search ............... None
See application file for complete search history.

(56) References Cited

U.S. PATENT DOCUMENTS

| 6,407,253 B1 | 6/2002 | Alami et al. |
|---|---|---|
| 2002/0128319 A1 | 9/2002 | Koo et al. |
| 2005/0089945 A1 | 4/2005 | Koo et al. |

FOREIGN PATENT DOCUMENTS

| EP | 0 338 291 | 3/1989 |
|---|---|---|
| EP | 1201 661 A | 5/2002 |
| FR | 2 193 611 A | 2/1974 |
| WO | WO 93/14056 | 7/1993 |
| WO | WO 01/47895 A | 7/2001 |

OTHER PUBLICATIONS

Smeyers et al. Journal of Pharmaceutical Sciences 1985, 74(1), 47-9.*
Citron, M. Nature Reviews Neuroscience 2004, 5, 677-685.*
Weggen, et al., "A Subset of NSAIDs Lower Amyloidogenic AB42 Independental of Cyclooxygenase Activity", Nature, vol. 414, pp. 212-216, Nov. 8, 2001.
Veld, et al., "Nonsteroidal Antinflammatory Drugs and The Risk of Alzheimer's Disease", The New England Journal of Medicine, vol. 345, No. 21, pp. 1515-1521, Nov. 22, 2001.
F. Clemence et al., "Recherche de composes anti-inflammatoires et analgesiques dans la serie du Thiophene", Chimica Therapeutica, vol. 9, No. 4, Jul. 1974, pp. 390-396.
M. Bellassoued et al. "Unexpected formation of 3,3a,4,7a-tetrahydrobenzofuran-2,5-diones as well as arene carboxylic acids . . . ", Chemical Communications, vol. 2, 1999, pp. 187-188.
J. B. Summers et al., "In vivo characterization of hydroxamic acid inhibitors of 5-lipoxygenase", Journal of Medicinal Chemistry, vol. 30, No. 11, 1987, pp. 2121-2126.

* cited by examiner

*Primary Examiner*—Rebecca Anderson
*Assistant Examiner*—Jason M Nolan
(74) *Attorney, Agent, or Firm*—William Krovatin; Raynard Yuro

(57) ABSTRACT

The present invention encompasses compounds of Formula I (I)

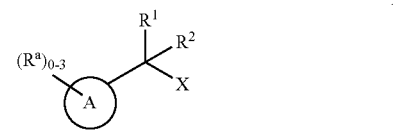

or pharmaceutically acceptable salts thereof, wherein A is the base molecule of a propionic acid or acetic acid NSAID, or a derivative thereof, X is $-CO_2H$, 1H-tetrazol-5-yl or 2H-tetrazol-5-yl and $R^1$ and $R^2$ are each independently selected from the group consisting of: $C_{1-6}$alkyl and $C_{3-6}$cycloalkyl, as well as pharmaceutical composition comprising said compounds and methods of using said compounds. The compounds of the present invention lower the level of $A\beta_{42}$ and are therefore useful for preventing, delaying or reversing the progression of Alzheimer's Disease.

7 Claims, No Drawings

GEMINALLY DI-SUBSTITUTED NSAID DERIVATIVES AS Aβ42 LOWERING AGENTS

CROSS REFERENCE TO RELATED APPLICATIONS

This application is a U.S. national Phase application under 35.U.S.C. § 371 of PCT Application No. PCT/US2004/000424, filed Jan. 9, 2004, which claims priority under 35 U.S.C. 119 to U.S. No. 60/439,847, filed Jan. 14, 2003 and U.S. No. 60/439,965, filed Jan. 14, 2003.

BACKGROUND OF THE INVENTION

Alzheimer's disease is a neurodegenerative disease of the brain leading to severely impaired cognition and functionality. This disease leads to progressive regression of memory and learned functions. Alzheimer's disease is a complex disease that affects cholinergic neurons, as well as serotonergic, noradrenergic and other central neurotransmitter systems. Manifestations of Alzheimer's disease extends beyond memory loss and include personality changes, neuromuscular changes, seizures, and occasionally psychotic features.

The defining pathological hallmarks of AD are the presence of neurofibrillary tangles and senile plaques in the brain. Amyloid β polypeptides (AP) are the major constituents of amyloid plaques and are derived from altered processing of amyloid precursor proteins (APPs). Aβ consists predominantly of two forms, $A\beta_{40}$ and $A\beta_{42}$. Although $A\beta_{40}$ is the predominant form, recent evidence suggests that $A\beta_{42}$ is the pathogenic form. In addition to $A\beta_{40}$ and $A\beta_{42}$, the processing of Aβ generates other Aβ forms such as $A\beta_{39}$, $A\beta_{38}$, $A\beta_{37}$, and $A\beta_{34}$.

The present invention encompasses geminally di-substituted derivatives of nonsteroidal anti-inflammatory drugs, which lower the level of $A\beta_{42}$ and are therefore useful for preventing, delaying or reversing the progression of Alzheimer's Disease. The compounds of the invention also have a reduced potency for cyclooxygenase activity and therefore do not possess the gastrointestinal side effects associated with nonsteroidal antiinflammatory drugs (NSAIDs).

SUMMARY OF THE INVENTION

The present invention encompasses compounds of Formula I

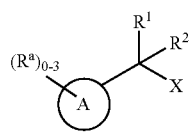

I or pharmaceutically acceptable salts thereof, wherein A is the base molecule of a propionic acid or acetic acid NSAID, or a derivative thereof, X is —$CO_2H$, 1H-tetrazol-5-yl or 2H-tetrazol-5-yl and $R^1$ and $R^2$ are each independently selected from the group consisting of: $C_{1-6}$alkyl and $C_{3-6}$cycloalkyl, as well as pharmaceutical composition comprising said compounds and methods of using said compounds. The compounds of the present invention lower the level of $A\beta_{42}$ and are therefore useful for preventing, delaying or reversing the progression of Alzheimer's Disease.

DETAILED DESCRIPTION OF THE INVENTION

The present invention encompasses a compound of Formula I

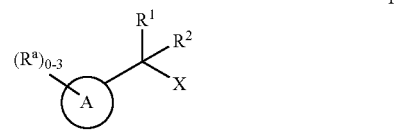

I or a pharmaceutically acceptable salt thereof, wherein:
X is —$CO_2H$, 1H-tetrazol-5-yl or 2H-tetrazol-5-yl;
each $R^a$ may be substituted at any substitutable position on A and each $R^a$ is independently selected from the group consisting of: fluoro, chloro, bromo, $NH_2$, methyl, ethyl, methoxy and $CF_3$;
$R^1$ and $R^2$ are each independently selected from the group consisting of: $C_{1-6}$alkyl and $C_{3-6}$cycloalkyl; and
A is selected from the group consisting of:

1)

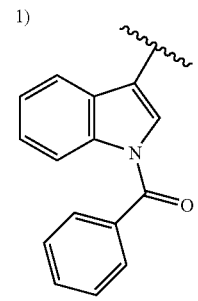

2)

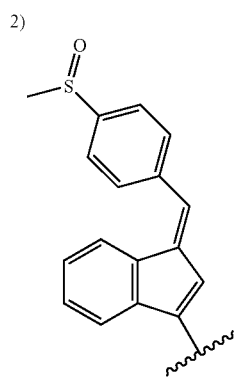

3)

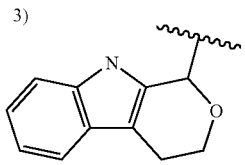

4)

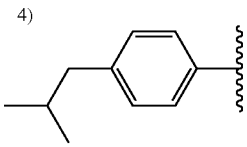

-continued
5) 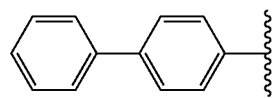
6) 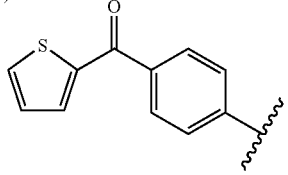
7) 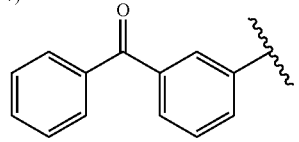
8) 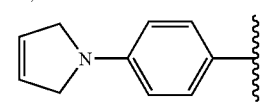
9) 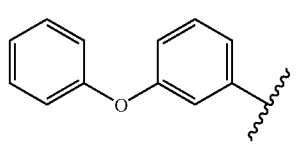
10) 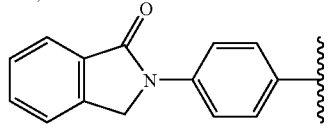
11) 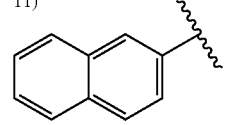
12) 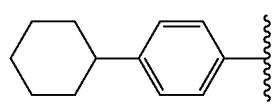
13) 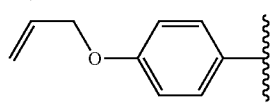
14) 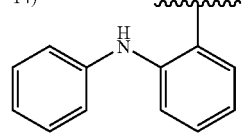
-continued
15) 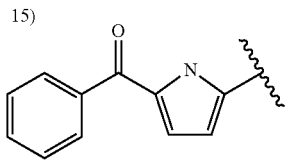
16) 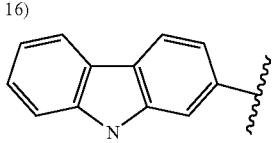
17) 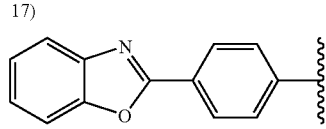
18) 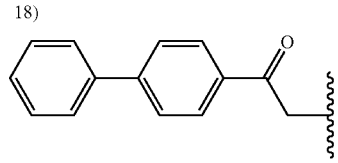
19) 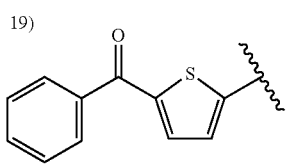
20) 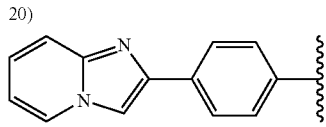
21) 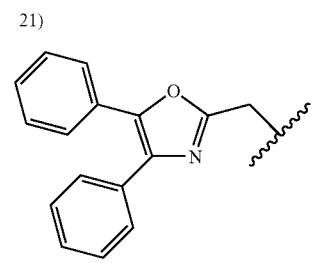
22) 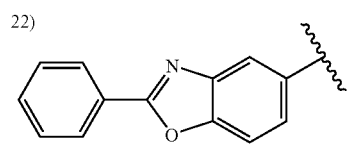
23) 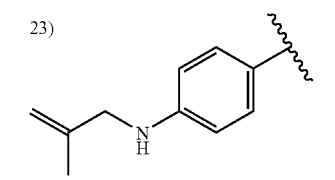

-continued
24)
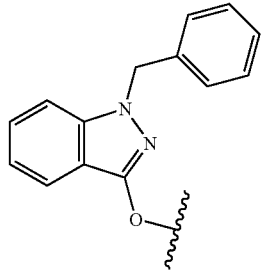
25)
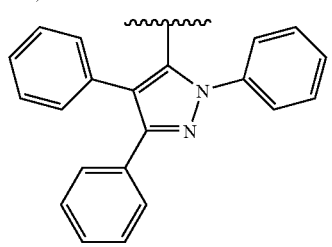
26)
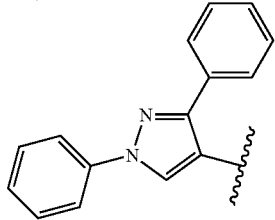
27)
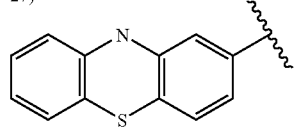
28)
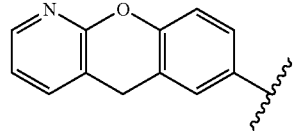
29)
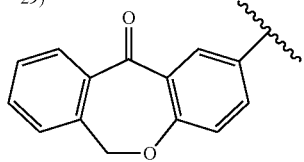
30)
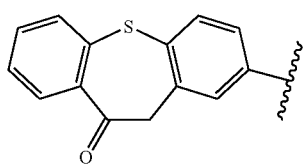
-continued
31)
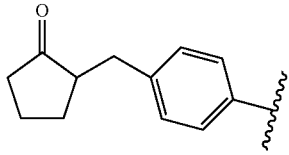
32)
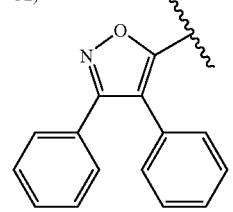
33)
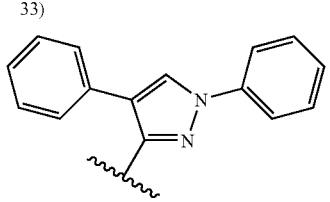
34)
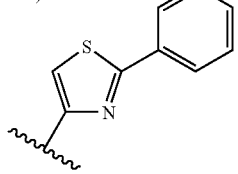
35)
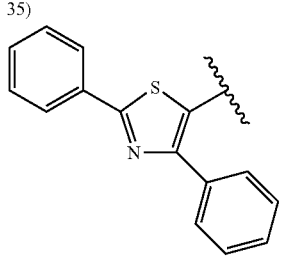
36)
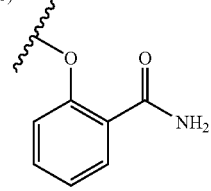
37)
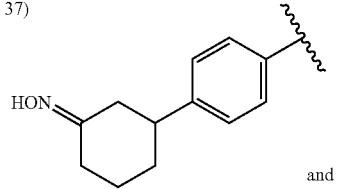
and -continued 38) 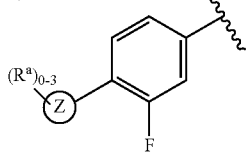

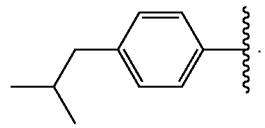

Within this embodiment is encompassed compounds of Formula I wherein no $R^a$ group is present. Also within this embodiment is encompass ed compounds of Formula I wherein $R^1$ and $R^2$ are each $C_{1-4}$alkyl.

Another embodiment of the invention encompasses a compound of Formula I wherein A is

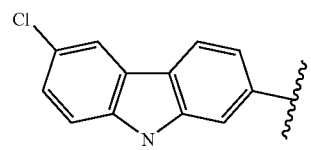

wherein for 38) above $R^a$ is substituted on A as shown and Z is selected from the group consisting of: phenyl, benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The point of attachment shown in 1) to 38) above is to the group —$(R^1)(R^2)$—X. $R^a$ may be substituted at any substitutable position on 1) to 38) above.

and wherein the two additional $R^a$ groups may be substituted at any substitutable position on A above. Within this embodiment is encompassed compounds of Formula I wherein no $R^a$ group is present. Also within this embodiment is encompassed compounds of Formula I wherein $R^1$ and $R^2$ are each $C_{1-4}$alkyl.

Another embodiment of the invention encompasses a compound of Formula I wherein A is

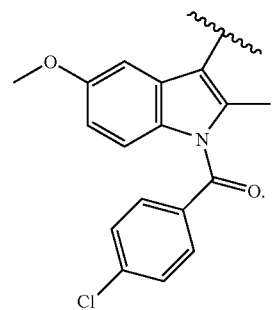

Another embodiment of the invention encompasses a compound of Formula I wherein $R^1$ and $R^2$ are each $C_{1-4}$alkyl.

An embodiment of the invention encompasses a compound of Formula I wherein $R^1$ and $R^2$ are each $C_{1-4}$alkyl.

Another embodiment of the invention encompasses a compound of Formula I wherein X is —$CO_2H$.

Another embodiment of the invention encompasses a compound of Formula I wherein X is 1H-tetrazol-5-yl or 2H-tetrazol-5-yl.

Another embodiment of the invention encompasses a compound of Formula I wherein A is Another embodiment of the invention encompasses a compound selected from the following group:

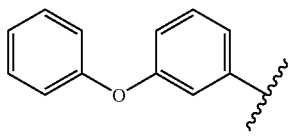

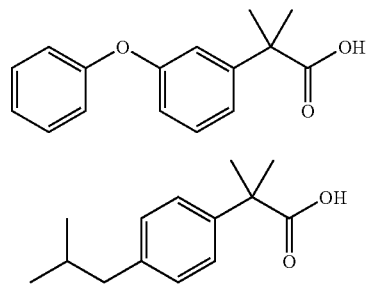

Within this embodiment is encompassed compounds of Formula I wherein no $R^a$ group is present. Also within this embodiment is encompassed compounds of Formula I wherein $R^1$ and $R^2$ are each $C_{1-4}$alkyl.

Another embodiment of the invention encompasses a compound of Formula I wherein A is

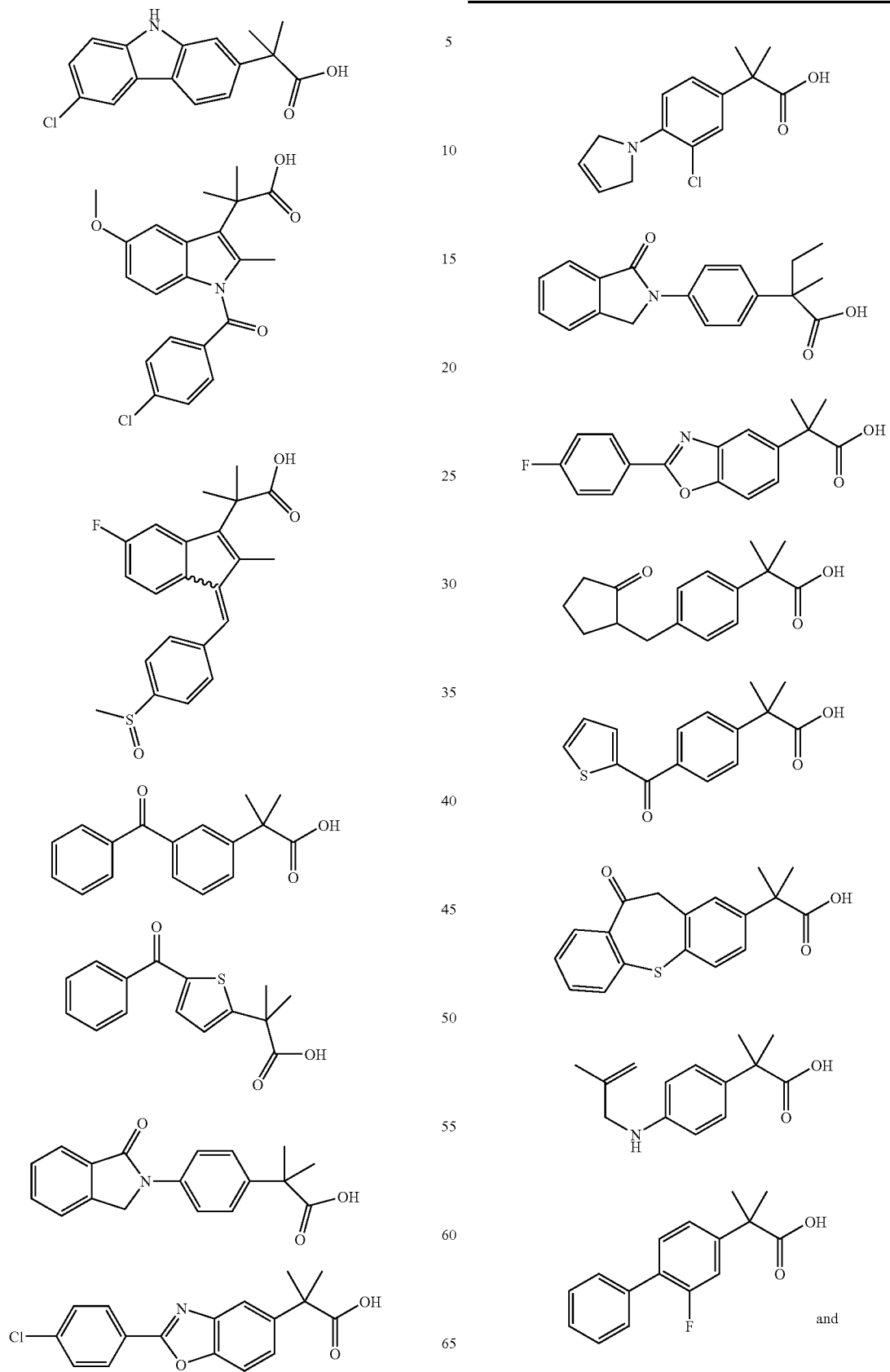

-continued

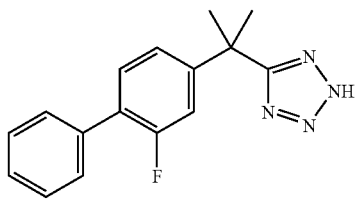

or a pharmaceutically acceptable salt of any of the above.

Another embodiment of the invention encompasses a compound of Formula I wherein $R^1$ and $R^2$ are each methyl.

Another embodiment of the invention encompasses a compound of Formula I wherein $R^1$ is methyl and $R^2$ is ethyl.

The invention also encompasses a pharmaceutical composition comprising a compound of Formula I in combination with a pharmaceutically acceptable carrier.

Another embodiment of the invention encompasses a method for preventing, delaying or reversing the progression of Alzheimer's Disease in a patient in need thereof comprising administering to said patient a compound of Formula I in amount that is effective for preventing, delaying or reversing the progression of Alzheimer's Disease.

Another embodiment of the invention encompasses a method for treating Alzheimer's Disease in a patient in need thereof comprising administering to said patient a compound of Formula I in amount that is effective for treating Alzheimer's Disease.

For purposes of this specification, when a nitrogen atom appears in structures for A in Formula I, it is understood that sufficient hydrogen atoms or $R^a$ groups are present to satisfy the valency of the nitrogen atom.

The term "alkyl" means linear or branched structures and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4propylnonyl, and the like.

The term "cycloalkyl" means cyclic structures, optionally combined with linear or branched structures, containing the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl and the like.

For purposes of this specification, the term "AD" is an abbreviation for Alzheimer's Disease.

One skilled in the art can readily identify patients in need of treatment for preventing, delaying or reversing the progression of Alzheimer's Disease. Clinical symptoms of AD include, for example, progressive disorientation, memory loss, and aphasia. Eventually, disablement, muteness, and immobility occur. Pathological indicators of AD include, for example, the presence of neurofibrillary tangles, neuritic plaques, and amyloid angiopathy. Preventing the progression of AD means preventing the onset or further development of clinical symptoms and/or pathological indicators of AD. For example, an individual who does not have clinical symptoms or pathological indicators of AD can be prevented from developing clinical symptoms or pathological indicators. Further, an individual who has a mild form of AD can be prevented from developing a more severe form of AD. Delaying the progression of AD means delaying the time of onset of AD-related symptoms and/or pathological indicators or slowing the rate of progression of AD, determined by the rate of development of clinical symptoms and pathological indicators. Reversing the progression of AD meanss lessening the severity of an AD condition, i.e., the AD condition of an individual has changed from severe to less severe as indicated by fewer clinical symptoms or pathological indicators.

An individual can choose to take an $A\beta_{42}$ lowering agent as a preventative measure to avoid developing AD. For example, an individual with a genetic predisposition to AD can take an $A\beta_{42}$ lowering agent to prevent or delay the development of AD. A genetic predisposition can be determined based on known methods. For example, an individual can be considered to have a genetic predisposition to AD if the individual has a family history of AD. Genetic predisposition to AD also can include point mutations in certain genes such as the APP gene, the presenilin-I or presenilin-2 gene, or the apolipoprotein E gene. Such mutations can predispose individuals to early-onset familial AD (FAD), increased risk of developing AD, or decreased age at onset of AD. (See page 1332, Table 30-2 of Cotran et al. (1999) *Robbins Pathologic Basis of Disease,* Sixth Edition, W.B. Saunders Company; and U.S. Pat. No. 5,455,169.) Furthermore, an individual who has clinical symptoms of, or has been diagnosed with, AD can take an $A\beta_{42}$ lowering agent to prevent or delay further progression of AD as well as to reverse the pathological condition of the disease.

An AD diagnosis can be made using any known method. Typically, AD is diagnosed using a combination of clinical and pathological assessments. For example, progression or severity of AD can be determined using Mini Mental State Examination (MMSE) as described by Mohs et al. (1996) *Int Psychogeriatr* 8:195-203; Alzheimer's Disease Assessment Scale-cognitive component (ADAS-cog) as described by Galasko et al. (1997) *Alzheimer Dis Assoc Disord,* 11 suppl 2:S33-9; the Alzheimer's Disease Cooperative Study Activities of Daily Living scale (ADCS-ADL) as described by McKhann et al. (1984) *Neurology* 34:939-944; and the NINCDS-ADRDA criteria as described by Folstein et al. (1975) *J Psychiatr Res* 12:189-198. In addition, methods that allow for evaluating different regions of the brain and estimating plaque and tangle frequencies can be used. These methods are described by Braak et al. (1991) *Acta Neuropathol* 82:239-259; Khachaturian (1985) *Arch Neuro* 42:1097-1105; Mirra et al. (1991) *Neurology* 41:479-486; and Mirra et al. (1993) *Arch Pathol Lab Med* 117:132-144.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

Pharmaceutical Compositions

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

A slow release pharmaceutical formulation can also be employed with the compounds of the present invention that may have a short half-life to provide a formulation that can be conveniently dosed on a once a day basis. Such slow-release formulations that can be utilized with the present invention are disclosed, for example, in WO 93/10771, published on Jun. 10, 1993.

Dosage Levels

Dosage levels of the order of from about 0.01 mg to about 140 mg/kg of body weight per day are useful in preventing, delaying or reversing the progression of Alzheimer's Disease, or alternatively about 0.5 mg to about 7 g per patient per day. For example, compounds of the present invention may be administered in amounts ranging from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Optical Isomers—Diastereomers

Compounds of formula I may contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I may be obtained by stereospecific synthesis using optically pure starting materials or reagents of known configuration.

Methods of Synthesis

As shown in Scheme 1, geminally di-substituted derivatives of NSAIDs are readily synthesized from the parent acid by standard Fischer esterification to afford the corresponding ester, which is then alkylated using a strong base, co-solvent, such as HMPA or DMPU, and appropriate alkylating agent. The ester is then hydrolyzed under standard conditions, or in a more facile manner, employing potassium trimethylsilanolate.

Scheme 1: General Scheme for alkylation of acidic NSAID's.

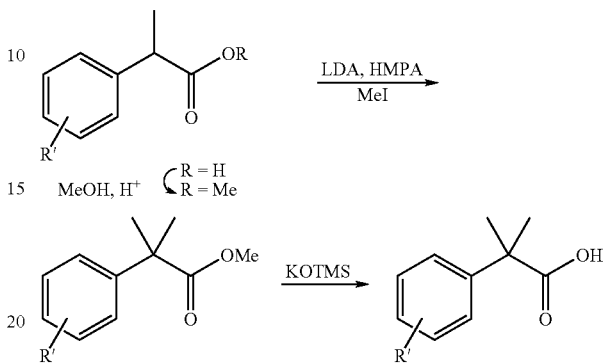

Methods that can be utilized for making geminally di-substituted derivatives of caprofen and indomethacin are shown on Schemes 2 and 3.

Scheme 2: Synthesis of Carprofen derivative.

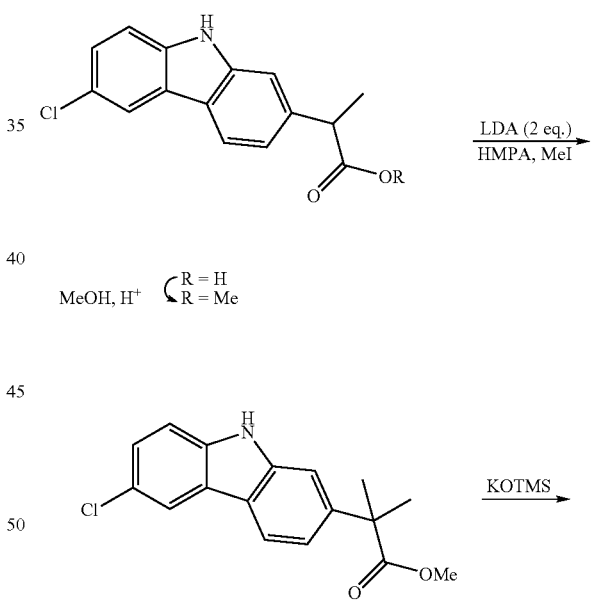

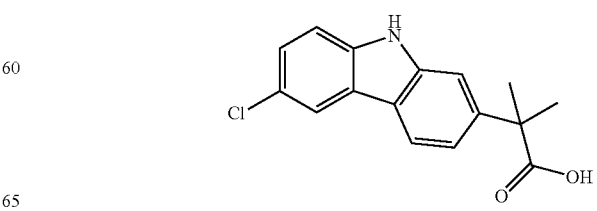

Scheme 3: Synthesis of Indomethacin derivative.

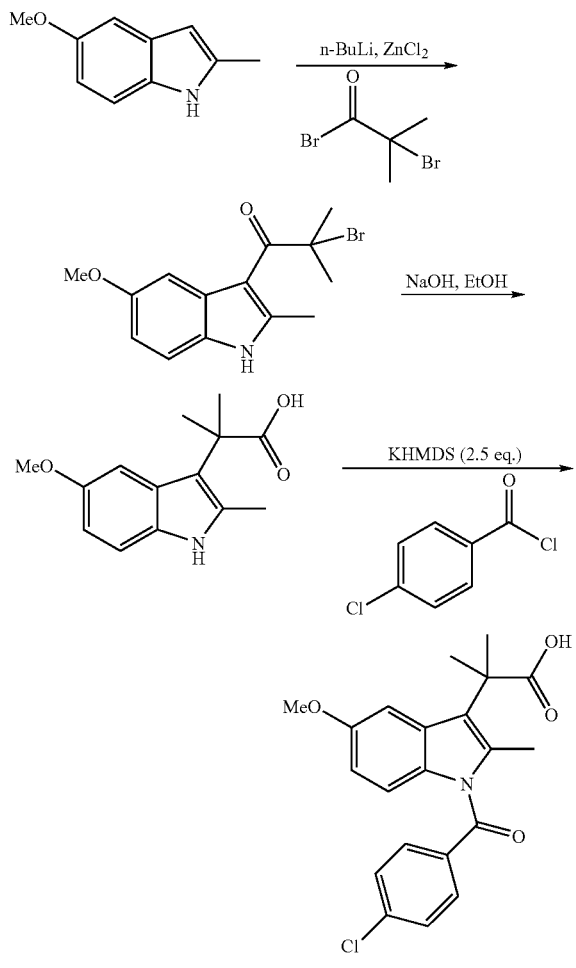

Methods for making flurbiprofen derivatives of Formula I wherein X is tetrazolyl can be made by following Scheme 4:

Scheme 4: Synthesis of flurbiprofen derivative

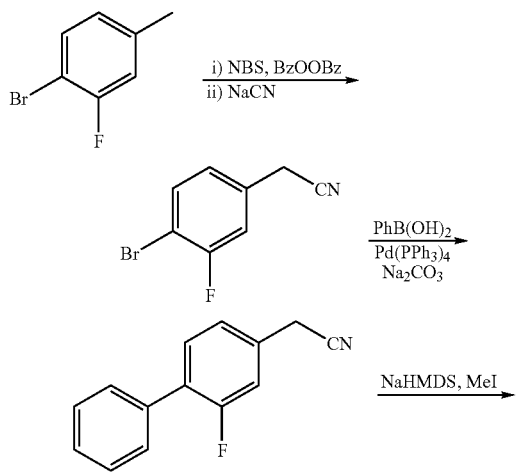

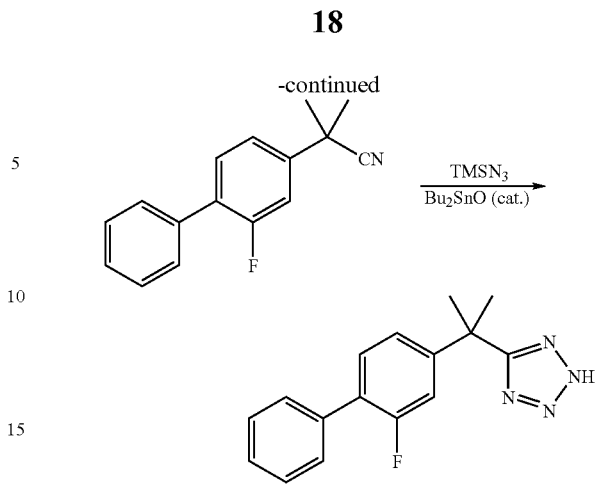

Methods for making other tetrazolyl derivatives of the invention are discernible from the above method by practitioners in the field.

REPRESENTATIVE EXAMPLES

The following non-limiting examples further exemplify the invention:

Example 1

2-(2-Fluoro-1,1'-biphenyl-4-yl)-2-methylpropanoic acid

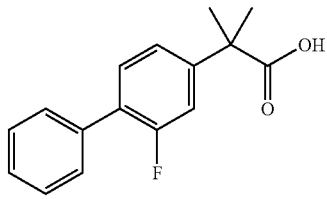

To 2-fluoro-α-methyl-4-biphenylacetic acid (5.00 g, 20.5 mmol) in methanol (120 mL) was added conc. $H_2SO_4$ (0.1 mL) and the resulting solution heated to reflux for 12 hr. After cooling, solid $NaHCO_3$ (~5 g) was added, the suspension stirred for 10 minutes and filtered. Evaporation of the filtrate to dryness, extraction of the residue with ethyl acetate (~100 mL), filtration and evaporation to dryness afforded the methyl ester as a colorless oil. $^1$H NMR (500 MHz, $CDCl_3$) δ 7.46 (2H, m), 7.26-7.38 (4H, m), 7.04-7.09 (2H, m), 3.68 (1H, q, J=7.2 Hz), 3.63 (3H, s), 1.46 (3H, d, J=7.2 Hz).

To a −78° C. cooled solution of the methyl ester (methyl 2-(2-fluoro-1,1'-biphenyl-4-yl)propanoate) (1.00 g, 3.87 mmol) in THF (7 mL) was added lithium diisopropylamide (0.64M soln in THF; 7.8 mL, 1.3 eq.) dropwise and the resulting orange/red solution stirred at −78° C. for 30 mm. Subsequent warming to 0° C. with an ice bath was followed by the addition of dry hexamethylphosphoramide (1 mL). After a further 30 min at 0° C., methyl iodide (482 μL, 7.74 mmol) was added in one portion whereupon complete dissipation of the red color was observed. Stirring was maintained for a further 30 min at which point satd. aq. $NH_4Cl$ soln. was added, the resulting slurry diluted in EtOAc (50 mL), the organic phase washed with water then brine and dried ($MgSO_4$). Evaporation of the filtrate to dryness yielded the desired alkylated product as a colorless oil. $^1$H NM (500 MHz, CDCl$_3$) δ 7.47 (2H, m), 7.29-7.38 (4H, m), 7.06-7.18 (2H, m), 3.62 (3H, s), 1.54 (6H, s).

To the isolated oil (200 mg, 0.734 mmol) in THF (2 mL) was added potassium trimethylsilanolate (90% technical grade; 110 mg; 0.771 mmol) and the solution heated to 45° C. for 2 hr. A further 70 mg of reagent was added and the heating continued for a further 30 min. The solution was allowed to cool, diluted with EtOAc (10 mL) and acidified with 0.5M HCl to ~pH 3. The organic layer was separated and the aqueous phase extracted with EtOAc. The combined organic phases were dried (MgSO$_4$), filtered and evaporated to dryness to afford the desired acid, 2-(2-fluoro-1,1'-biphenyl-4-yl)-2-methylpropanoic acid, as a colorless powder. $^1$H NMR (500 MHz, CDCl$_3$) δ 7.53 (2H, m), 7.45-7.35 (4H, m), 7.26-7.21 (2H,m), 1.64 (6H, s).

Example 2

2-Methyl-2-(3-phenoxy-phenyl)-propionic acid

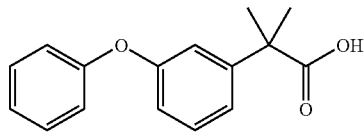

To a suspension of calcium 2-(3-phenoxy-phenyl)-propionate hydrate (5.00 g, 9.57 mmol) in methanol (150 mL) was added conc. H$_2$SO$_4$ (1.1 mL) and the gelatinous solution heated to reflux for 4 hrs. After cooling, the solution was filtered and evaporated to dryness, the residue dissolved in EtOAc, washed with satd. aq. NaHCO$_3$ soln., dried (MgSO$_4$) and evaporated to yield methyl-2-(3-phenoxy-phenyl)-propionate as a colorless oil. $^1$H NMR (500 MHz, CDCl$_3$) δ 7.34 (2H, m), 7.26 (1H, m), 7.11 (1H, m), 6.99-7.02 (4H, m), 6.87 (1H, m), 3.70 (1H, q, J=7.2 Hz), 3.67 (3H, s), 1.58 (3H, d, J=7.2 Hz)

To a solution of methyl-2-(3-phenoxy-phenyl)-propionate (1.00 g; 3.90 mmol) in THF (7 mL) cooled to −78° C. was added lithium diisopropylamide (0.64M soln in THF; 7.8 mL, 1.3 eq.) dropwise and the resulting solution stirred at −78° C. for 30 min. Subsequent warming to 0° C. with an ice bath was followed by the addition of dry hexamethylphosphoramide (1 mL) and after a further 30 min at 0° C., methyl iodide (482 µL, 7.74 mmol) was added in one portion. Stirring was maintained for a further 1 hr at which point satd. aq. NH$_4$Cl soln. was added, the resulting slurry diluted in EtOAc (50 mL), the organic phase washed with water then brine and dried (MgSO$_4$). Evaporation of the filtrate to dryness yielded the desired alkylated product as a colorless oil. $^1$H NMR (500 MHz, CDCl$_3$) δ 7.33 (2H, m), 7.27 (1H, m), 6.80-7.13 (5H, m), 6.86 (1H, m), 3.65 (3H, s), 1.55 (6H, s)

To a solution of methyl 2-methyl-2-(3-phenoxy-phenyl)-propionate (712 mg, 2.63 mmol) in THF (8 mL) was added potassium trimethylsilanolate (90% technical grade; 563 mg; 1.5 eq) and the solution heated to 45° C. for 5 hrs. The solution was allowed to cool, diluted with EtOAc (15 mL) and acidified with 2M HCl to ~pH 3. The organic layer was separated and the aqueous phase extracted with EtOAc. The combined organic phases were dried (MgSO$_4$), filtered and evaporated to dryness to afford the desired acid, 2-methyl-2-(3-phenoxy-phenyl)-propionic acid, as a colorless powder. $^1$H NMR (500 MHz, CDCl$_3$) δ 7.25-7.35 (3H, m), 7.08-7.16 (3H, m), 7.01 (2H, dd, J=7.7, 0.6 Hz), 6.86 (1H, dd, J=8.1, 2.3 Hz), 1.58 (6H, s).

Example 3

2-(4-Isobutyl-phenyl)-2-methyl-propionic acid

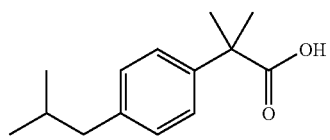

To a solution of 2-(4-isobutyl-phenyl)-propionic acid (5.00 g, 24.2 mmol) in anhydrous MeOH (150 mL) was added conc H$_2$SO$_4$ (catalytic) and heated to reflux for 5 hrs. After cooling, the solution was evaporated to dryness, the residue dissolved in methylene chloride, dried (MgSO$_4$), filtered and evaporated to yield methyl 2-(4isobutyl-phenyl)-propionate as a colorless oil. $^1$H NMR (500 MHz, CDCl$_3$) δ 7.19 (2H, d, J=8,1 Hz), 7.09 (2H, d, J=8.1 Hz), 3.71 (1H, q, J=7.2 Hz), 3.66 (3H, s), 2.44 (2H, d, J=7.2 Hz), 1.84 (1H, app. septet, J=6.7 Hz), 1.48 (3H, d, J=7.2 Hz), 0.90 (6H, d, J=6.6 Hz).

To a solution of methyl 2-(4-isobutyl-phenyl)-propionate (1.00 g; 4.54 mmol) in THF (8 mL) cooled to −78° C. was added lithium diisopropylamide (0.64M soln in THF; 9.25, 1.3 eq.) dropwise and the resulting solution stirred at −78° C. for 30 min. Subsequent warming to 0° C. with an ice bath was followed by the addition of dry hexamethylphosphoramide (1 mL) and after a further 30 min at 0° C., methyl iodide (565 µL, 9.08 mmol) was added in one portion. Stirring was maintained for a further 1 hr at which point satd. aq. NH$_4$Cl soln. was added, the resulting slurry diluted in EtOAc (50 mL), the organic phase washed with water then brine and dried (MgSO$_4$). Evaporation of the filtrate to dryness yielded the desired alkylated product as a colorless oil. $^1$H NMR (500 MHz, CDCl$_3$) δ 7.23 (2H, d, J=8.3 Hz), 7.09 (2H, d, J=8.3 Hz), 3.65 (3H, s), 2.44 (2H, d, J=7.2 Hz), 1.85 (1H, app. septet, J=6.8 Hz), 1.56 (6H, s), 0.90 (6H, d, J=6.6 Hz).

To a solution of the previously isolated oil (666 mg, 2.84 mmol) in THF (9 mL) was added potassium trimethylsilanolate (90% technical grade; 608 mg; 1.5 eq) and the solution heated to 45° C. for 5 hrs. The solution was allowed to cool, diluted with EtOAc (15 mL) and acidified with 2M HCl to ~pH 3. The organic layer was separated and the aqueous phase extracted with EtOAc. The combined organic phases were dried (MgSO$_4$), filtered and evaporated to dryness to afford the desired acid, 2-(4-isobutyl-phenyl)-2-methyl-propionic acid, as a colorless powder. $^1$H NMR (500 MHz, CDCl$_3$) δ 7.31 (2H, d, J=8.2 Hz), 7.11 (2H, d, J=8.2 Hz), 2.45 (2H, d, J=7.2 Hz), 1.85 (1H, app. septet, J=6.8 Hz), 1.59 (6H, s), 0.90 (6H, d, J=6.6 Hz).

Example 4

2-(6-Chloro-9H-carbazol-2-yl)-2-methyl-propionic acid

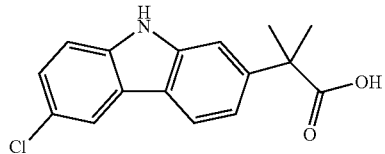

To a methanolic solution (50 mL) of 2-(6-chloro-9H-carbazol-2-yl)-propionic acid (356 mg, 1.30 mmol) was added conc. H$_2$SO$_4$ (catalytic) and the mixture heated to reflux for 12 hrs. The solution was evaporated to dryness and the residue purified by column chromatography (0 to 20% EtOAc:Hexanes) to afford the methyl ester as a colorless oil. $^1$H NMR (500 MHz, CDCl$_3$) δ 8.16 (1H, s), 7.98 (1H, d, J=1.3 Hz), 7.94 (1H, d, J=8.1 Hz), 7.27-7.36 (3H, m), 7.17 (1H, d, J=8.1 Hz), 3.89 (1H, q, J=7.1 Hz), 3.69 (3H, s), 1.59 (3H, d, J=7.1 Hz).

To a −78° C. cooled solution of methyl 2-(6-chloro-9H-carbazol-2-yl)-propionate (353 mg, 1.23 mmol) in THF (3 mL) was added lithium diisopropylamide (0.64M soln in THF; 4.04 mL, 2.1 eq.) dropwise and the resulting solution stirred at −78° C. for 30 min. Subsequent warming to 0° C. with an ice bath was followed by the addition of dry hexamethylphosphoramide (1 mL) and after a further 30 min at 0° C., methyl iodide (84.2 μL, 1.35 mmol) was added in one portion. Stirring was maintained for a further 1 hr at which point satd. aq. NH$_4$Cl soln. was added, the resulting slurry diluted in EtOAc, the organic phase washed with water and dried (MgSO$_4$). Evaporation of the filtrate and purification of the residue by column chromatography (0 to 20% EtOAc:hexanes) afforded the desired alkylated product along with a small amount of the bis-alkylated carbazole. (major product) $^1$H NMR (500 MHz, CDCl$_3$) δ 8.06 (1H, s), 7.98 (1H, d, J=1.0 Hz), 7.95 (1H, d, J=8.2 Hz), 7.40 (1H, m), 7.34 (2H, m), 7.23 (1H, dd, J=8.5, 1.5 Hz), 3.66 (3H, s), 1.67 (6H, s).

To a solution of methyl 2-(6-Chloro-9H-carbazol-2-yl)-2-methyl-propionate in THF (1.5 mL) was added potassium trimethylsilanolate (189 mg, 2.5 eq) and the mixture heated to 50° C. for 3 hrs. The solution was diluted with EtOAc and acidified to ~pH 3 with 2M HCl. The organic layer was separated and the aqueous phase extracted with EtOAc. The combined organic phases were dried (MgSO$_4$), filtered and evaporated to dryness to afford the desired acid, 2-(6-chloro-9H-carbazol-2-yl)-2-methyl-propionic acid, as a colorless solid. $^1$H NMR (500 MHz, MeOD) δ 7.98 (1H, d, J=1.8 Hz), 7.96 (1H, d, J=8.1 Hz), 7.47 (1H, d, J=1.5 Hz), 7.37 (1H, d, J=8.6 Hz), 7.29 (1H, dd, J=8.6, 2.1 Hz), 7.21 (1H, d, J=8.4, 1.7 Hz), 1.63 (6H, s).

Example 5

2-[1-(4-Chloro-benzoyl)-5-methoxy-2-methyl-1H-indol-3-yl]-2-methyl-propionic acid

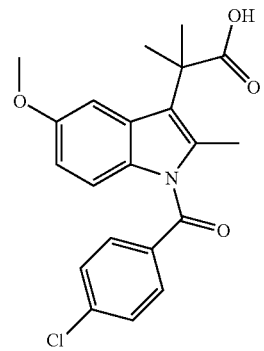

To an ice-cooled solution of 5-methoxy-2-methylindole (2.5 g, 15.5 mmol) in THF (30 mL) was added n-butyl-lithium (2.5M solution in hexanes: 6.25 mL, 16.28 mmol) in a dropwise manner. After 20 minutes, ZnCl$_2$ (1M solution in ether; 15.5 mL, 1.0 eq.) was added and the resulting solution stirred at 0° C. for 2 hrs. The solvent was then removed and the residue dissolved in anhydrous toluene (30 mL) to which 2-bromoisobutyryl bromide (1.93 mL, 16.28 mmol) was added and the mixture stirred at ambient temperature for 24 hrs. The solution was partitioned between 1M HCl (100 mL) and EtOAc (100 mL), the organic phase separated, washed with water, dried (MgSO$_4$), filtered and evaporated to dryness. The residue was purified by column chromatography (0 to 25% EtOAc:hexanes) to afford 2.0 g of 2-bromo-1-(5-methoxy-2-methyl-1H-indol-3-yl)-2-methyl-propan-1-one as a yellow solid. $^1$H NMR (500 MHz, CDCl$_3$) δ 8.52 (1H, s), 7.97 (1H, d, J=2.2 Hz), 7.21 (1H, d, J=8.8 Hz), 6.87 (1H, dd, J=8.8, 2.2 Hz), 3.91 (3H, s), 2.67 (3H, s), 2.13 (6H, s).

To a solution of NaOH (1.6 g) in EtOH (13.4 mL) and water (3.3 mL) was added the above bromide (500 mg; 1.61 mmol) in small portions over the period of 1 hr. The solution was concentrated and the residue partitioned between NaHCO$_3$ soln (3:1 water:satd. aq. NaHCO$_3$ soln.) and diethyl ether. The organic layer was extracted with dilute NaHCO$_3$ solution a further two times and the aqueous layer acidified with 4M HCl to pH 3 with caution. Extraction of the acidic aqueous with diethyl ether (×3), drying (MgSO$_4$), filtration and evaporation yielded 2-(5-methoxy-2-methyl-1H-indol-3-yl)-2-methyl-propionic acid as an orange foam. $^1$H NMR (500 MHz, CDCl$_3$) δ 7.64 (1H, s), 7.13 (1H, d, J=8.7 Hz), 7.07 (1H, d, J=2.2 Hz), 6.77 (1H, dd, J=8.7, 2.2 Hz), 3.74 (3H, s), 2.44 (3H, s), 1.75 (6H, s). LCMS(EI) 248 (M+H)$^+$.

To an ice-cooled solution of 2-(5-methoxy-2-methyl-1H-indol-3-yl)-2-methyl-propionic acid (150 mg, 0.611 mmol) in THF (4 mL) was added KHMDS (0.5M solution in toluene; 3.1 mL, 1.55 mmol) and the solution stirred for 20 min at 0° C. 4-Chlorobenzoyl chloride (85.4 uL, 0.672 mmol) was added and the solution allowed to attain ambient temperature. After 30 minutes, satd. aq. NH$_4$Cl soln. was added and the aqueous layer acidified with dil. HCl, extracted with EtOAc, the organic phase dried (MgSO$_4$), filtered and evaporated. The residue was purified by column chromatography (0 to 30% acetone:hexanes) to afford 2-[1-(4-chlorobenzoyl)-5-methoxy-2-methyl-1H-indol-3-yl]-2-methyl-propionic acid as an orange foam. $^1$H NMR (500

MHz, CDCl₃) δ 7.69 (2H, d, J=8.4 Hz), 7.46 (2H, d, J=8.4 Hz), 7.08 (1H, d, J=2.4 Hz), 6.91 (1H, d, J=9.0 Hz), 6.66 (1H, dd, J=9.0, 2.4 Hz), 3.74 (3H, s), 2.39 (3H, s), 1.79 (6H, s). LCMS(EI) 386 (M+H)⁺.

Example 6

5-[1-(2-Fluoro-biphenyl-4-yl)-1-methyl-ethyl]-2H-tetrazole

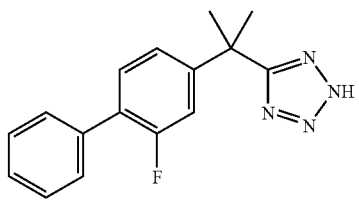

A solution of 1-bromo-2-fluoro-4-methyl-benzene (5.0 g, 26.45 mmol), N-bromosuccinimide (4.94 g, 27.75 mmol) and benzoyl peroxide (100 mg) in carbon tetrachloride (75 mL) was heated under reflux for 3 hrs, allowed to cool, filtered and the residue flashed through a plug of silica gel, eluting with hexanes. The solvent was evaporated to dryness to afford a colorless oil. The crude product (1.73 g, 6.46 mmol) and sodium cyanide (317 mg, 6.46 mmol) was heated to reflux in a mixture of ethanol (17 mL) and water (3 mL) for a period of 4 hrs. After cooling, the solution was evaporated to dryness and the residue purified by column chromatography (0 to 10% EtOAc in hexanes) to afford (4-bromo-3-fluoro-phenyl)-acetonitrile as a pale orange solid. ¹H NMR (500 MHz, CDCl₃) δ 7.56 (1H, m), 7.12 (1H, d, J=8.9 Hz), 7.02 (1H, d, J=8.9 Hz), 3.73 (3H, s).

A biphasic mixture of water (3 mL) and toluene (10 mL) containing (4-bromo-3-fluoro-phenyl)-acetonitrile (457 mg, 2.14 mmol), sodium carbonate (1.00 g, 9.45 mmol), phenyl boronic acid (781 mg, 6.41 mmol) was sparged with nitrogen for 10 min, tetrakis(triphenylphosphine)palladium (250 mg) was added and the mixture heated to reflux for 48 hrs. After cooling, the solution was diluted with EtOAc, washed with water, the organic phase dried (MgSO₄), filtered and evaporated to dryness. The residue was purified by column chromatography (0 to 10% EtOAc in hexanes) to afford (2-fluoro-biphenyl-4-yl)-acetonitrile as a colorless solid. ¹H NMR (500 MHz, CDCl₃) δ 7.54 (2H, m), 7.46 (3H, m), 7.40 (1H, m), 7.17 (2H, m), 3.79 (3H, s).

To the previously isolated biphenyl (328 mg, 1.55 mmol) in dry THF (7 mL) was added NaHMDS (1.0M solution in THF; 3.41 mL, 3.41 mmol) dropwise at 0° C. After 15 minutes, methyl iodide (212 µL, 3.41 mmol) was added and the solution allowed to warm to ambient temperature. Subsequent to stirring for 2 hrs, the reaction mixture was quenched upon addition of satd. aq. NH₄Cl soln., diluted with EtOAc and washed with water. The organic phase was separated, dried (MgSO₄), filtered and evaporated to dryness. The residue was purified by column chromatography (0 to 10% EtOAc in hexanes) to afford 2-(2-fluoro-biphenyl-4-yl)-2-methyl-propionitrile. 1H NMR (500 MHz, CDCl₃) δ 7.55 (2H,m), 7.47 (3H, m), 7.40 (1H, m), 7.36 (1H, m), 7.27 (1H, m), 1.77 (6H, s).

A mixture of 2-(2-fluoro-biphenyl-4-yl)-2-methyl-propionitrile (100 mg, 0.418 mmol), azidotrimethylsilane (222 µL, 1.672 mmol) and dibutyltin oxide (20 mg) in dry toluene (2.5 mL) was heated under microwave irradiation in a sealed vessel at 150° C. for 1000 seconds. The solution was then diluted with EtOAc, washed with water, the organics separated, dried (MgSO₄), filtered and evaporated to dryness. The residue was purified by column chromatography (EtOAc) to afford the title compound, 5-[1-(2-Fluoro-biphenyl-4-yl)-1-methyl-ethyl]-2H-tetrazole as a colorless powder. ¹H NMR (500 MHz, CD₃OD) δ 7.50 (2H, m), 7.40-7.46 (3H, m), 7.35 (1H, m), 7.05-7.12 (2H, m), 1.87 (6H, s). LCMS(EI) 283.1 (M+H)⁺, 324.2 (M+Na+H₃O)⁺.

Further compounds of the invention are exemplified in the following table:

| Ex. | Structure |
| --- | --- |
| 7 | ![structure 7] |
| 8 | ![structure 8] |
| 9 | ![structure 9] |
| 10 | ![structure 10] |
| 11 | ![structure 11] |
| 12 | ![structure 12] |

-continued

| Ex. | Structure |
|---|---|
| 13 | (isoindolin-1-one N-phenyl 2-methylbutanoic acid structure) |
| 14 | (4-fluorophenyl benzoxazole 2-methylpropanoic acid structure) |
| 15 | (cyclopentanone-methyl phenyl 2-methylpropanoic acid structure) |
| 16 | (thiophene-2-carbonyl phenyl 2-methylpropanoic acid structure) |
| 17 | (dibenzothiepinone 2-methylpropanoic acid structure) |
| 18 | (methallylamino phenyl 2-methylpropanoic acid structure) |

Assays for Determining Biological Activity

Protocol for Measuring Aβ 1-40 and 1-42 Levels:

Day 1:
SHSY5Y neuroblastoma cells (ATCC), overexpressing the beta secretease-cleaved form of APP, are grown to about 50%-60% confluency. Alternatively, CHO or HEK cells overexpressing $APP_{695}$ could be used (Beheret. al., *J. Neurochem.* 2002).

Change media on cells and add Sodium Butyrate (10 mM) for ~4 hours before harvesting, counting and plating cells to 96-well plates at 35 000 cells/well in 100 μL of MEM (without HEPES and phenol red) plus 10% PBS (heat treated), 50 mM HEPES, 1% Glutamine. (induction not needed for CHOs or HKs).

Take 200 mM stock of compounds for testing and dilute in DMSO to give final concentrations of 60, 20, 6 & 2 mM in 100% DMSO.

Dilute 10 μL of these diluted compounds to 182 μL with compound dilution media [MEM (without HEPES and phenol red) plus 50 mM HEPES, 1% Glutamine]

Add 10 μL of this dilution to the cells 1-2 hours after plating. To the cells in wells A1-D1 and E12 to H12, add 10 μL, 5.5% DMSO in compound dilution media. To wells A12-D12 add 10 μL, 2 mM L-685458 in 5.5% DMSO/compound dilution media.

Incubate overnight at 37° C., 5% $CO_2$.

Day 2:
The Origen ECL system (Igen Europe Inc., UK) is used for the read-out. Website: http://www.igen.com/jumppage-.htm catalog #310800

Make up appropriate Origen antibody mixes as follows:
Aβ40: 2.75 ml Origen Buffer, 1 μg/ml Ru-G2-10 (,4 μg/ml 4G8-Bio per plate (Clarke and Shearman, *J. Neuroscience Methods,* 2000)

Aβ42: 2.75 ml Origen Buffer, 0.5 μg/ml Ru-G2-11, 4 μg/ml 4G8-Bio per plate (Clarke and Shearman, *J. Neuroscience Methods,* 2000)

Remove 10 μl of media to fresh Origen plate for Aβ40 measurement along with 40 μl of Origen Buffer (PBS, 2% BSA, 0.2% Tween-20). *Stock of origen buffer must be a maximum of a couple of days old.

Remove 50 μl of media to fresh Origen plate for Aβ42 measurement.

Add 25 μl of appropriate Origen Mix to plates and store plates at 4° C. overnight on shaker.

To the cells and remaining media add 5 μL 10×MTS/PES before returning to incubator. Mix then read plates at 492 nm after ~4 hours.

(N.B. For other cell lines, check plates after 30 mins. CHO & HEK cells rapidly convert the yellow MTS mixture to brownish-purple formazan. Ideally, absorbance should be 0.3-0.6 units)

Day 3:
Calibrate Origen plate reader.
Make up Streptavidin Dynabead Premix as follows:
Aβ40 and Aβ42: 400 μg/ml (110 μl) Streptavidin Dynabeads in 2.75 ml Origen Buffer per plate.

Add 25 μl of Bead Premix per well and incubate at room temperature for 15 minutes on shaker. (if several plates, stagger start times to ensure 15 minute incubation.)

Fill all wells with 150 μl of Origen Buffer (250 μl in any empty wells)

Read plates on Origen reader (Takes ~10 minutes per plate)

Compounds of the present invention were demonstrated to preferentially lower the levels of $Aβ_{42}$ relative to the level of $Aβ_{40}$ utilizing the assay conditions described above and are therefore useful for preventing, delaying or reversing the progression of Alzheimer's Disease.

In another embodiment, the present invention encompasses a-compound of Formula I'

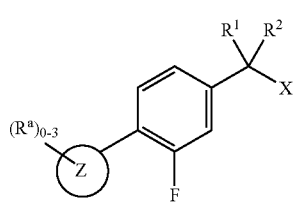

I' or a pharmaceutically acceptable salt thereof, wherein:
Z is selected from the group consisting of: phenyl, benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, X is —$CO_2H$, 1H-tetrazol-5-yl or 2H-tetrazol-5-yl, $R^1$ and $R^2$ are each independently ethyl or methyl, and each $R^a$ is independently selected from the group consisting of: fluoro, chloro, bromo, $NH_2$, methyl, ethyl, methoxy and $CF_3$.

An embodiment of the invention encompasses a compound of Formula I' wherein Z is phenyl.

Another embodiment of the invention encompasses a compound of Formula I' wherein $R^a$ is not present.

Another embodiment of the invention encompasses a compound of Formula I' wherein $R^1$ and $R^2$ are each methyl.

Another embodiment of the invention encompasses a compound of Formula I' wherein X is —$CO_2H$.

Another embodiment of the invention encompasses a compound of Formula I' wherein X is 1H-tetrazol-5-yl or 2H-tetrazol-5-yl.

Another embodiment of the invention encompasses a compound of Formula I' wherein $R^a$ is selected from the group consisting of: fluoro, chloro and bromo.

Another embodiment of the invention encompasses a compound of Formula I'a

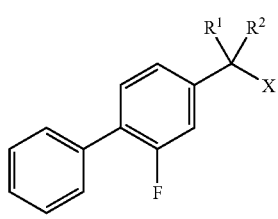

I'a or a pharmaceutically acceptable salt thereof, wherein:
X is —$CO_2H$, 1H-tetrazol-5-yl or 2H-tetrazol-5-yl and
$R^1$ and $R^2$ are each independently ethyl or methyl.

Another embodiment of the invention encompasses a pharmaceutical composition comprising a compound of Formula I' in combination with a pharmaceutically acceptable carrier.

Another embodiment of the invention encompasses a method for preventing, delaying or reversing the progression of Alzheimer's Disease in a patient in need thereof comprising administering to the patient a compound of Formula I' in amount that is effective for preventing, delaying or reversing the progression of Alzheimer's Disease.

Another embodiment of the invention encompasses a method for treating Alzheimer's Disease in a patient in need thereof comprising administering to said patient a compound of Formula I' in amount that is effective for treating Alzheimer's Disease.

What is claimed is:

1. A method for treating Alzheimer's Disease in a patient in need thereof comprising administering to said patient a compound of Formula I

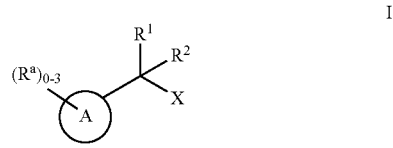

I or a pharmaceutically acceptable salt thereof, wherein:
X is —$CO_2H$, 1H-tetrazol-5-yl or 2H-tetrazol-5-yl;
each $R^a$ may be substituted at any substitutable position on A and each $R^a$ is independently selected from the group consisting of: fluoro, chloro, bromo, $NH_2$, methyl, ethyl, methoxy and $CF_3$;
$R^1$ and $R^2$ are each independently selected from the group consisting of: $C_{1-6}$alkyl and $C_{3-6}$cycloalkyl; and
A is selected from the group consisting of:

1)

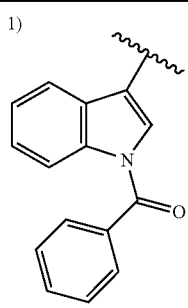

2)

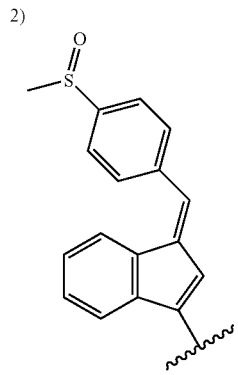

3)

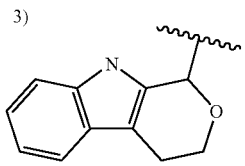

-continued
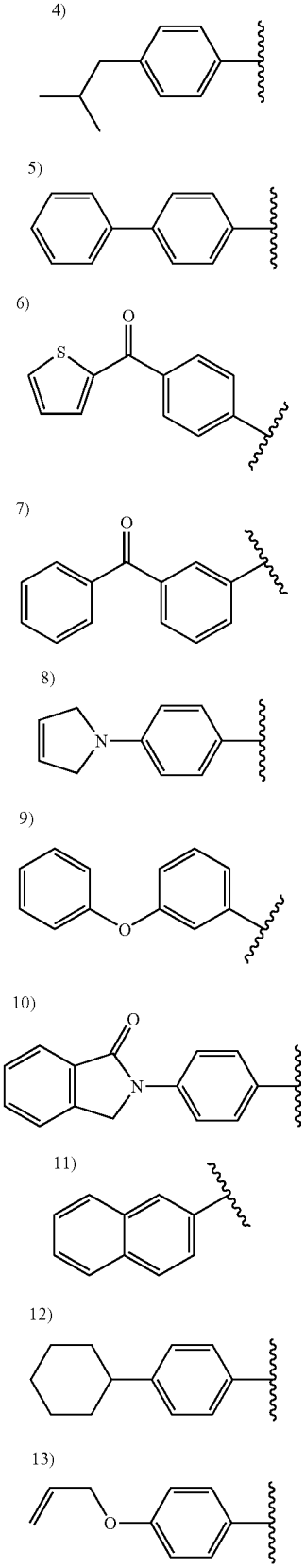
-continued
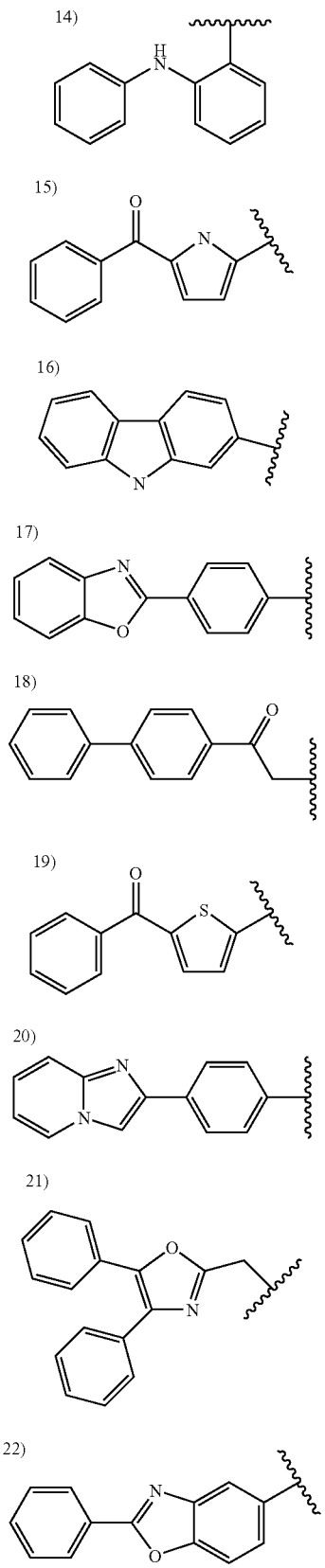

-continued
23) 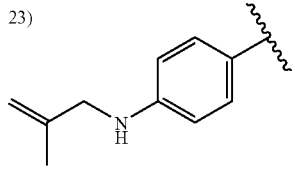
24) 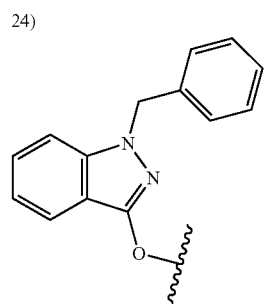
25) 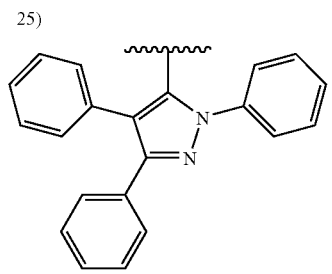
26) 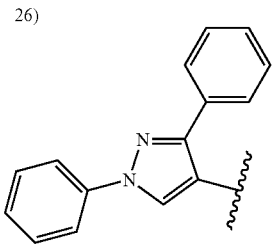
27) 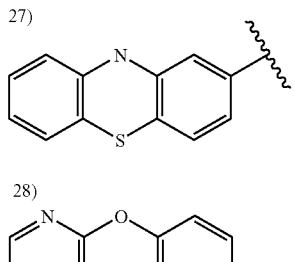
28) 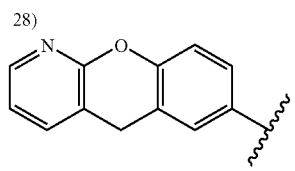
29) 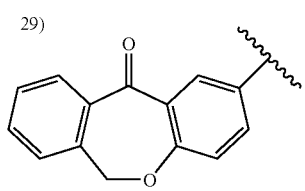
-continued
30) 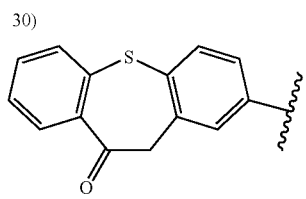
31) 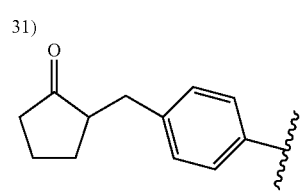
32) 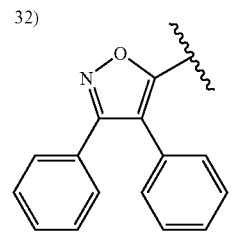
33) 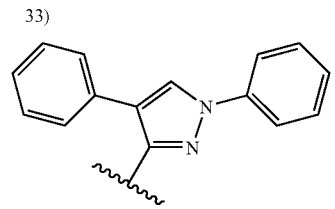
34) 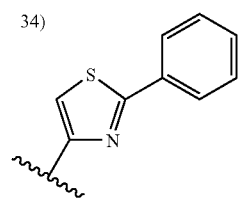
35) 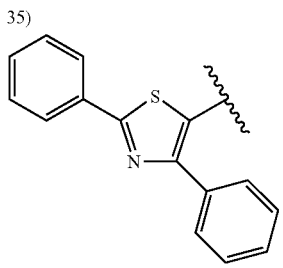
36) 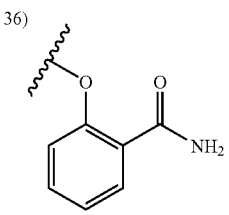

-continued

37)
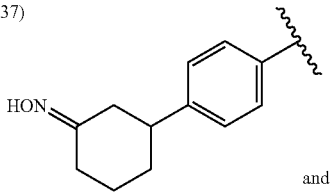

and

38)
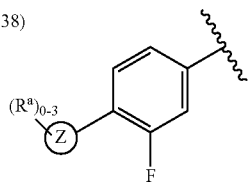

wherein for 38) above $R^a$ is substituted on A as shown and Z is selected from the group consisting of: phenyl, benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, in amount that is effective for treating Alzheimer's Disease.

2. A method for treating Alzheimer's Disease in a patient in need thereof comprising administering to said patient a compound of Formula I'

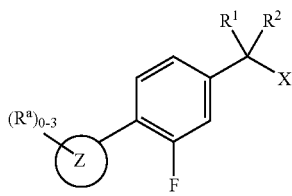

I' or a pharmaceutically acceptable salt thereof, wherein:

Z is selected from the group consisting of: phenyl, benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, X is —$CO_2H$, 1H-tetrazol-5-yl or 2H-tetrazol-5-yl, $R^1$ and $R^2$ are each independently ethyl or methyl, and each $R^a$ is independently selected from the group consisting of: fluoro, chloro, bromo, $NH_2$, methyl, ethyl, methoxy and $CF^3$, in amount that is effective for treating Alzheimer's Disease.

3. The method for treating Alzheimer's Disease in a patient in need thereof in accordance with claim 1 comprising administering to said patient a compound of Formula I wherein $R^1$ and $R^2$ are each $C_{1-4}$alkyl and all other variables are as previously defined in amount that is effective for treating Alzheimer's Disease.

4. The method for treating Alzheimer's Disease in a patient in need thereof in accordance with claim 3 comprising administering to said patient a compound of Formula I wherein $R^1$ and $R^2$ are each methyl and all other variables are as previously defined in amount that is effective for treating Alzheimer's Disease.

5. The method for treating Alzheimer's Disease in a patient in need thereof in accordance with claim 1 comprising administering to said patient a compound of Formula I wherein X is —$CO_2H$ and all other variables are as previously defined in amount that is effective for treating Alzheimer's Disease.

6. A method for treating Alzheimer's Disease in a patient in need thereof in accordance with claim 1 comprising administering to said patient a compound of Formula I selected from the following group:

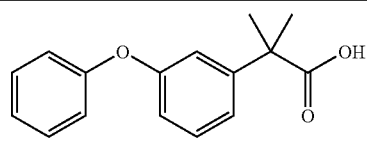

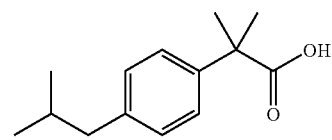

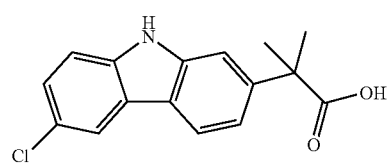

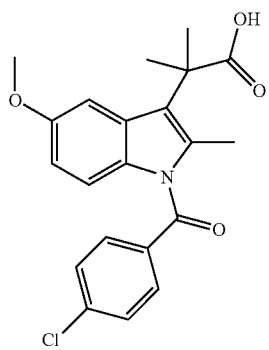
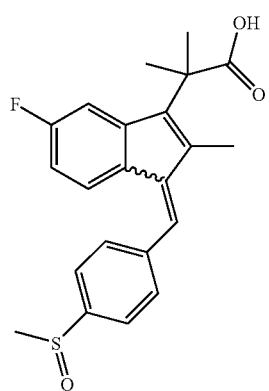
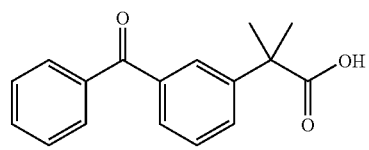
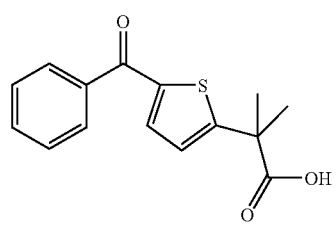
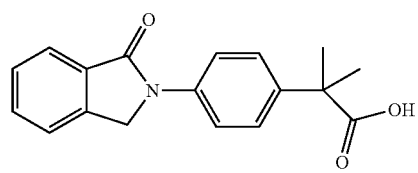
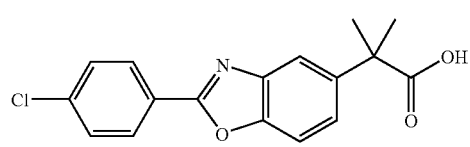
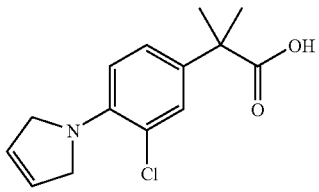
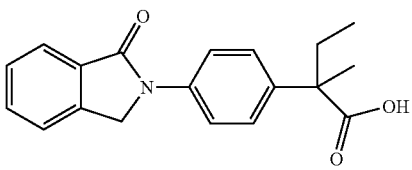
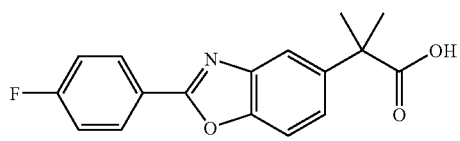
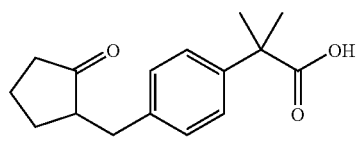
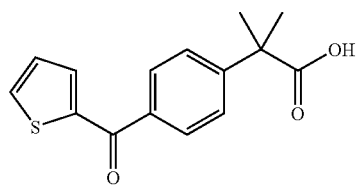
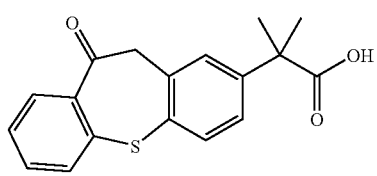
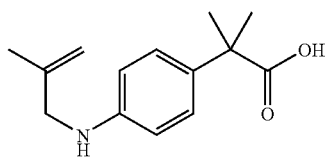
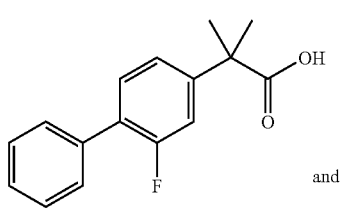
and -continued

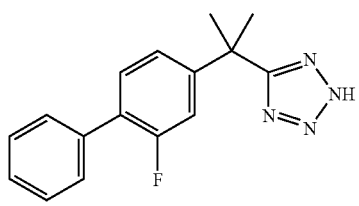

or a pharmaceutically acceptable salt of any of the above, in amount that is effective for treating Alzheimer's Disease.

7. The method for treating Alzheimer's Disease in a patient in need thereof in accordance with claim 2 comprising administering to said patient a compound of Formula I'a

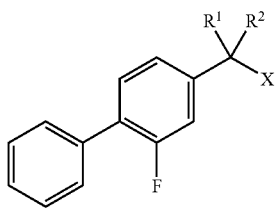

or a pharmaceutically acceptable salt thereof, wherein:
X is —$CO_2H$, 1H-tetrazol-5-yl or 2H-tetrazol-5-yl and
$R^1$ and $R^2$ are each independently ethyl or methyl, in amount that is effective for treating Alzheimer's Disease.

* * * * *